United States Patent [19]

Kato et al.

[11] Patent Number: 5,023,339
[45] Date of Patent: Jun. 11, 1991

[54] STABILIZED MALEIMIDE COMPOSITION AND PROCESS FOR PREPARING SAME

[75] Inventors: Kenji Kato; Nariyoshi Koga; Yukinori Haruta, all of Oita, Japan

[73] Assignee: Nippon Oil and Fats Co., Ltd., Tokyo, Japan

[21] Appl. No.: 446,266

[22] Filed: Dec. 5, 1989

[51] Int. Cl.$^5$ ............ C07D 207/448; C07D 207/452; C08F 22/40
[52] U.S. Cl. .................................................. 548/401
[58] Field of Search ........................................ 548/401

[56] References Cited

U.S. PATENT DOCUMENTS 4,083,798 4/1978 Versteeg .............................. 424/19
4,383,062 5/1983 Saad ...................................... 524/35

Primary Examiner—Mark L. Berch
Attorney, Agent, or Firm—Jordan and Hamburg

[57] ABSTRACT

A maleimide compound of high stability contains 5 to 70 wt. % of a maleimide compound represented by the formula of

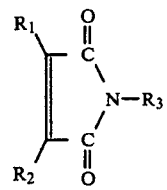

wherein $R_1$ and $R_2$ each stand for a hydrogen atom, a halogen atom or a methyl group, $R_3$ stands for a straight-chained or branched alkyl group having 1 to 18 carbon atoms, a halogen-substituted straight-chained alkyl group having 1 to 18 carbon atom, a cycloalkyl group having 3 to 12 carbon atoms or an aryl or aralkyl group having 6 to 18 carbon atoms, 0.1 to 20 wt. % of a surfactant, 0.1 to 10 wt. % of a protective colloid and the balance of water.

9 Claims, No Drawings

STABILIZED MALEIMIDE COMPOSITION AND PROCESS FOR PREPARING SAME

BACKGROUND OF THE INVENTION

This invention relates to a maleimide composition and a process for preparing the same.

Maleimide compounds are generally solid at ambient temperature, so that they are used in the form of powders, hydrated powders or flakes However, the powdered state of the maleimide compounds gives rise in actual operation to an increased number of operating steps and to worsened operability at the time of metering and charging. Also the maleimide compounds exhibit sublimating properties and hence are unsatisfactory hygienically.

Heretofore, as a method for preparing an aqueous suspension of maleimide compounds, there is known a method by Japanese Laid-open Patent Application No.30157/1979 which consists in pulverizing the maleimide compounds to fine powders with the mean particle size of not more than 0.5 μm and mixing and dispersing the powders in a surfactant and water. However, with this method, a special equipment is required to pulverize the maleimide compounds to a particle size of not more than 0.5 μm, while the problem of working environment and pollution is presented on account of the necessity of disposing of dusts and dirts. There are also many other defects that remain to be solved, viz. that the aqueous suspension of the maleimide compounds is insufficient in storage stability, and that quaternary ammonium salts and amines not only decompose peroxides as a radical polymerization initiator rapidly by ionic decomposition, but also tend to lower thermal resistance and electrical properties of polymers appreciably.

SUMMARY OF THE INVENTION

It is a principal object of the present invention to provide a maleimide composition excellent in storage stability and highly convenient in metering and charging operations and for transport, above all, for transport by pumping, and a method for preparing the same.

It is another object of the present invention to provide a highly stable maleimide composition for heat-resistant resins capable of stabilizing polymer systems and preventing the lowering of the physical properties of produced polymers, and a method for preparing the same.

It is still another object of the present invention to provide a method for preparing a stable aqueous suspension of the maleimide compound easily in a shorter time period which is fully satisfactory from the environmental and hygienic aspects and in which there is no necessity of providing a special pulverizing equipment.

The above and other objects of the invention will become apparent from the following description.

According to the present invention, there is provided a maleimide composition of high stability comprising
(a) 5 to 70 wt.% of a maleimide compound represented by the formula (I)

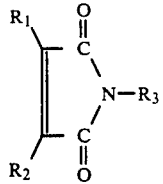

wherein $R_1$ and $R_2$ each stand for a hydrogen atom, a halogen atom or a methyl group, $R_3$ stands for a straight-chained or branched alkyl group having 1 to 18 carbon atoms, a halogen-substituted straight-chained alkyl group having 1 to 18 carbon atoms, a cycloalkyl group having 3 to 12 carbon atoms or an aryl or aralkyl group having 6 to 18 carbon atoms;
(b) 0.1 to 20 wt.% of a surfactant;
(c) 0.1 to 10 wt.% of a protective colloid; and
(d) a balance of water.

According to the present invention, there is also provided a method for preparing a maleimide composition comprising mixing and stirring the maleimide compound, the surfactant, the protective colloid and the water at a temperature of not lower than a dissolving temperature of the maleimide compound to produce an aqueous emulsion of the maleimide compound and cooling the aqueous emulsion.

PREFERRED EMBODIMENTS OF THE INVENTION

The present invention will be explained in more detail hereinbelow.

According to the present invention, there is employed a maleimide compound represented by the formula (I)

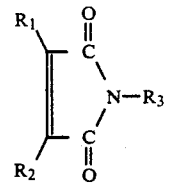

wherein $R_1$ and $R_2$ each stand for a hydrogen atom, a halogen atom or a methyl group, $R_3$ stands for a straight-chained or branched alkyl group having 1 to 18 carbon atoms, a halogen-substituted straight-chained alkyl group having 1 to 18 carbon atoms, a cycloalkyl group having 3 to 12 carbon atoms or an aryl or aralkyl group having 6 to 18 carbon atoms. If the number of carbon atoms exceeds the above limit values, manufacture becomes prohibitively difficult.

The maleimide compound represented by the formula (I) may include for example N-methyl maleimide, N-ethyl maleimide, N-n-propyl maleimide, N-n-butyl maleimide, N-t-butyl maleimide, N-i-butyl maleimide, N-n-pentyl maleimide, N-n-hexyl maleimide, N-cyclohexyl maleimide, N-n-heptyl maleimide, N-n-octyl maleimide, N-n-decyl maleimide, N-2-ethylhexyl maleimide, N-n-dodecyl maleimide, N-n-tetradodecyl maleimide, N-n-hexadecyl maleimide, N-lauryl maleimide, N-myristyl maleimide, N-hexadecyl maleimide, N-octadecyl maleimide, N-phenyl maleimide, N-(2-methyl)phenyl maleimide, N-(4-t-butyl)phenyl maleimide, N-cumyl maleimide, N-(3-methyl)phenyl maleimide, N-(4-methyl)phenyl maleimide, N-(2-ethyl)phenyl maleimide, N-(2-chloro)phenyl maleimide, N-(3-chloro)phenyl maleimide, N-(4-chloro)phenyl maleimide, N-(2,4-dichloro)phenyl maleimide, N-(2-bromo)phenyl maleimide, N-(2-fluoro)phenyl maleimide, N-benzyl maleimide, N-methylbenzyl maleimide, N-methyl-α-chloromaleimide, N-methyl-α-methylmaleimide, N-methyl-α-bromomaleimide, N-methyl-α-fluoromaleimide, N-cyclohexyl-α-chloromaleimide, N-cyclohexyl-α-bromomaleimide, N-cyclohexyl-α,8-dichloromaleimide, N-cyclohexyl-α-methylmaleimide, N-phenyl-α-chloromaleimide, N-phenyl-α-methylmaleimide, N-benzyl-α-chloromaleimide and N-benzyl-α-methylmaleimide. These maleimide compounds may be used alone or as a mixture of two or more of the compounds.

According to the present invention, the compositional ratio of the maleimide compound in the composition is 5 to 70 wt.%, preferably 5 to 60 wt.% and more preferably 10 to 50 wt.%. The above compositional ratio of less than 5 wt.% is not desirable because of elevated costs caused by the low concentration of the maleimide compound and because sufficient modification cannot be achieved on copolymerization. The above compositional ratio in excess of 70 wt.% is also not desirable because of markedly increased viscosity and increased handling difficulties.

According to the present invention, any of anionic, cationic or nonionic surfactants may be employed as the surfactants. The anionic surfactants may preferably be enumerated by aliphatic acid salts, such as sodium oleate, or castor oil potassium soap; sulfonates, such as alkyl sulfonates, sodium dodecylbenzene sulfonates, alkylnaphthalene sulfonates, derivatives of naphthalene sulfonates, sodium salts of β-naphthalene sulfonic acid formalin condensates, α-olefin sulfonates, or N-acyl sulfonates; higher alcohol sulfuric acid ester salts, such as sodium cetylsulfates or lauryl alcohol sodium sulfates; high molecular surfactants, such as polyoxyethylene alkyl ether sulfates, polyoxyethylene alkyl phenol ether sulfates, or polycarboxylic acid; phosphates such as alkyl phosphates, alkyl ether phosphates, or alkyl allyl ether phosphoric acids; sulfosuccinates such as dialkyl sulfosuccinates or dialkylesters of sodium sulfosuccinates; acylated amino compounds such as N-acylamino acid salts or acylated peptides; carboxylates such as alkyl ether carboxylates; sulfates such as alkylamide sulfates and sodium alkylmethyl taurine.

The cationic surfactants may preferably be enumerated by alkylamine hydrochlorates, alkyltrimethyl ammonium chlorides, alkyldimethylbenzyl ammonium chlorides and polyoxyethylene alkyl amines.

The nonionic surfactants may preferably be enumerated by alkyl polyoxyethylene ethers, such as polyoxyethylene stearyl ether; alkyl aryl polyoxyethylene ethers, such as polyoxyethylene nonyl phenol ethers or polyoxyethylene alkylphenyl ethers; alkylaryl formaldehydes condensed polyoxyethylene ethers; block and graft polymers having polyoxypropylene as oleophilic group; polyoxyethylene ethers of glycerin esters; sorbitan esters, such as lauric acid sorbitan esters, oleic acid sorbitan esters, palmitic acid sorbitan esters, polyoxyethylene sorbitan fatty acid esters or sorbitan monooleate; polyoxyethylene ethers of sorbitan esters; polyoxyethylene ethers of sorbitol esters; polyethyleneglycol fatty acid esters; glycerin esters, such as glycerin fatty acid esters or polyoxyethylene glycerin fatty acid esters; polyglycerin esters; propyleneglycol esters, such as propyleneglycol fatty acid esters; mono-, di- and trisaccharide fatty acid esters, such as lauric acid saccharose esters, palmitic acid saccharose esters, stearic acid saccharose esters or oleic acid saccharose esters; polyoxyethylene polyoxypropylene block polymers; fatty acid alkanolamides; and polyoxyethylene fatty acid amides.

According to the present invention, the compositional ratio of the surfactant in the maleimide composition is 0.1 to 20 wt.% and preferably 0.2 to 10 wt.%. The above compositional ratio of less than 0.1 wt.% is not desirable since dispersibility of the maleimide compound is markedly lowered, whereas the compositional ratio of higher than 20 wt.% is also not desirable, because uneconomical, since dispersing properties are not improved. One or more of the surfactants may be selectively employed as a function of the viscosity and storage stability of the maleimide composition.

If the anionic and/or nonionic surfactants are used as the surfactants, the resulting composition may be directly used as a comonomer for suspension or emulsion copolymerization with vinyl chloride, vinyl acetate, styrene, esters of acrylic acid or esters of methacrylic acid, since no cationic components are contained, so that there is no risk of the polymer system becoming unstable or the physical properties of the produced polymer being lowered.

The protective colloids employed in the present invention may preferably be enumerated by water-soluble cellulose derivatives, such as carboxymethyl cellulose, methyl cellulose, ethyl cellulose or hydroxyethyl cellulose; partially or completely saponified polyvinyl acetate, polyvinyl pyrrolidone, polyacrylic acids, acrylic acid amides, acrylic acid copolymers of acrylic acid esters, carboxyvinyl polymers, gelatine, starch and agar. One or more of the above mentioned protective colloids may be suitably selected as a function of the types of the above mentioned maleimide compounds and the desired viscosity of the aqueous suspensions of the present invention. The compositional ratio of the protective colloid in 100 wt.% of the aqueous suspension is 0.1 to 10 wt.%. For realizing moderate viscosity and stability, the above compositional ratio is in the range of from 0.2 to 5 wt.%. With the compositional ratio of less than 0.1 wt.%, a sufficiently stable aqueous suspension cannot be produced, whereas, with the compositional ratio of higher than 10 wt.%, the viscosity of the aqueous suspension is undesirably increased to present handling problems.

According to the present invention, the compositional ratio of water in the maleimide composition is such that the water forms the balance of the composition depending on the compositional ratios of the maleimide compound, the protective colloids and the surfactants.

For preparing the maleimide composition according to the present invention, one or more of the protective colloids and one or more of the surfactants are dissolved or dispersed in water to produce an aqueous phase, into which one or more of the above mentioned maleimide compounds are mixed to produce a mixture, which is then mixed and stirred at a temperature of not lower than the dissolving temperature of the maleimide compounds to produce an aqueous emulsion of the maleimide compounds. The dissolving temperature of the maleimide compounds herein means a temperature at which the maleimide compound or compounds are dissolved uniformly in the emulsion and is not necessarily coincident with a melting point of the maleimide compounds. For example, a mixture of a plurality of different maleimide compounds, plasticizers and solvents may be dissolved uniformly at a temperature lower than the melting point of the maleimide compound alone. Although it is sufficient if the stirring time in the above mixing and stirring is such that the particle size of the maleimide compound becomes sufficiently fine, the stirring time is preferably not longer than 20 minutes and more preferably not longer than 10 minutes. The stirring time longer than 20 minutes is not desirable because the polymerization reaction is brought about partially depending on the types of the maleimide compounds to form by-product oligomers. The mean particle size of the maleimide compound in the aqueous emulsion produced by the above mentioned mixing and stirring is preferably not more than 30 μm and more preferably not more than 10 μm for producing a particularly stable aqueous suspension. The above mentioned mean particle size in excess of 30 μm is not desirable since the particles then undergo precipitation or creaming.

According to the present invention, for producing an aqueous suspension of the maleimide compound from the above mentioned aqueous emulsion, the latter is stirred preferably for 30 to 60 minutes in the state of the aqueous emulsion and cooled approximately to room temperature to produce the aqueous suspension of the maleimide compounds. The cooling time of less than 30 minutes is not desirable since oil drops of the maleimide compounds dispersed into the produced aqueous suspension are not cooled sufficiently and, when left as they are, tend to be contacted with other oil drops to form droplets having non-uniform particle size so that such droplets are precipitated. If the state of dispersion of the produced aqueous suspension is insufficient, the above mentioned surfactants may be added further and stirred to produce a uniform dispersion system.

According to the present invention, stirrers employed or effecting the above mentioned series of the mixing and stirring operations may be enumerated by a forced rotation type stirrers provided with paddle-, propeller- or turbine blades, line mixers, high speed shearing devices, ultrasonic homogenizers, three-shaft type roll mills or ball mills.

The maleimide composition of the present invention may be prepared without the necessity of providing a special pulverizing equipment. Since the maleimide compounds may be turned into an emulsion in the presence of water, sublimation or turning into dusts and dirts of the maleimide compound may be prevented with definite advantages in environmental hygienics. The produced maleimide composition is excellent in storage stability and may be handled conveniently for transport by pumping or automatic metering. When the anionic surfactants and/or nonionic surfactants are used as the surfactants, the maleimide composition having superior industrial properties may be provided for use with resins exhibiting high thermal resistance.

EXAMPLES OF THE INVENTION

The present invention will be explained hereinafter by referring to Examples and Comparative Examples. It is noted, however, that these Examples are given only for the sake of illustration and should not be interpreted in the limiting sense.

EXAMPLE 1

680 grs. of water were charged into a beaker having capacity of 2 lit., into which were further charged 10 grs. of "NEWREX" R, a commercial name of sodium dodecylbenzene sulfonate produced by NIPPON OIL AND FATS CO., LTD., and 10 grs. of "GOSENOL" KH 17, a commercial name of a partially saponified polyvinyl acetate produced by NIPPON GOSEI KAGAKU KOGYO CO., LTD., and the resulting mass was stirred and dispersed by a ball mill. 300 grs. of N-cyclohexyl maleimide powders were added to the dispersion and stirred for 15 minutes. The resulting milk-white product was ball-milled at room temperature for 30 minutes for homogenization to produce an N-cyclohexyl maleimide-containing composition. The composition is shown in Table 1.

EXAMPLES 2 TO 12

N-substituted maleimide containing compositions were produced in the same way as in Example 1 except changing the kinds and the amounts of the N-substituted maleimides, the kinds and the amounts of the protective colloids and the equipments employed for homogenization. The compositions are shown in Table 1.

COMPARATIVE EXAMPLES 1 TO 3

N-substituted maleimide-containing compositions were prepared in the same way as in Example 1 except not using the protective colloid. The compositions are shown in Table 1.

EXAMPLE 13

With respect to the compositions of the present invention prepared by the Examples 1 to 12 and the compositions prepared by the Comparative Examples 1 to 3, measurements of the viscosity and the mean particle size of the N-substituted maleimides and tests on storage stability were conducted in the following manner.

The mean particle size of the N-substituted maleimide in each composition was measured by a particle size distribution measuring device manufactured by SEISHIN KIGYO CO., LTD. under the trade name of "MICRON PHOTOSIZER-SKC-2000". The viscosity was measured using a B-type viscometer under the conditions of 25° C. and the rotational speed of 20 r.p.m. Further, with regard to storage stability, each composition was placed in a test tube with an inside diameter of 18 mm and a length of 18 cm, to a level of 15 cm from the bottom, and each test tube was placed stationarily in an incubator maintained at 25° C. The time which elapsed until water was separated by not less than 1 cm from the liquid surface was measured. The results are shown in Table 2.

TABLE 1

| | | Ex. | | | | | | | | | | | | Comp. Ex. | | |
| --- | --- | --- | --- | --- | --- | --- | --- | --- | --- | --- | --- | --- | --- | --- | --- | --- |
| | | 1 | 2 | 3 | 4 | 5 | 6 | 7 | 8 | 9 | 10 | 11 | 12 | 1 | 2 | 3 |
| N-substituted Maleimides | N-cyclohexyl-maleimide | 300 | 400 | | | | | | | | | | 150 | 300 | | 100 |
| | N-methylmaleimide | | | 100 | | | | | | | | | | | | | |
| | N-(2-ethylhexyl) | | | | 400 | | | | | | | | | | | | |

TABLE 1-continued

| | | | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 | Comp. Ex. 1 | Comp. Ex. 2 | Comp. Ex. 3 |
|---|---|---|---|---|---|---|---|---|---|---|---|---|---|---|---|---|---|
| | | maleimide | | | | | | | | | | | | | | | |
| | | N-octadecyl-maleimide | | | | | 500 | | | | | | | | | | |
| | | N-phenylmaleimide | | | | 50 | | 600 | | | | | 150 | | | 50 | |
| | | N-(2-chloro)phenylmaleimide | | | | | | | | 400 | | | | | | | |
| | | N-benzylmaleimide | | | | | | | | | 300 | | | | | | |
| | | N-cyclohexyl-α-chloromaleimide | | | | | | | | | | 300 | | | | | |
| | | N-cyclohexyl-α-methylmaleimide | | | | | | | | | | | 300 | | | | |
| Surfactants | Anionic | *¹PERSOFT SK | | 10 | | 30 | 100 | | | | | 10 | | | | | |
| | | *¹NEWREX R | 10 | | 2 | | | 0.5 | 100 | | | | | | | | |
| | | *¹TRACKS K-300 | | | | | | | | 5 | | | 50 | 10 | 10 | 5 | |
| | Nonionic | *¹NONION NS-206 | | 10 | | | | | | 3 | 20 | 50 | | | | | |
| | | *¹NONION SP-60R | | | | 30 | | 0.5 | 100 | | | 5 | 5 | | | | |
| | Cationic | *¹CATION BB | | | | | | | | | | | | | | | 5 |
| Protective Colloids | | Methyl Cellulose | | | 2 | | 80 | | | | 5 | | 5 | | | | |
| | | Carboxymethyl Cellulose | | | | 30 | | | | | | 5 | | 2 | | | |
| | | *²GOSENOL KH 17 | 10 | 10 | | | | 1 | 20 | 5 | | | | | | | |
| | | Water | 680 | 470 | 896 | 510 | 320 | 948 | 180 | 587 | 675 | 680 | 595 | 683 | 690 | 945 | 895 |
| | | Dispersing Device | Ball Mill | | | Colloid Mill | | | | Homogenizer (Ultrasonic) | | | | | Ball Mill | | |

Note: The figures in the Table are given in units of grams.

*¹
PERSOFT SK: Sodium Alkylsulfate
NEWREX R: Sodium Dodecylbenzene Sulfonate
TRACKS K-300: Special Anionic Ion
NONION NS-206: Polyoxyethylene Nonyl Phenyl Ether
NONION SP-60R: Sorbitan Monostearate
CATION BB: Dodecyl Trimethyl Ammonium Chloride (Mfd. by NIPPON OIL & FATS CO., LTD.)
*²Partially Saponified Polyvinyl Acetate (Mfd. by NIPPON GOSEI KAGAKU KOGYO CO., LTD.)

TABLE 2

| | Mean Particle Size of N-substituted Maleimide (μ) | Viscosity of Each Sample (Poise) | Storage Stability of Each Sample |
|---|---|---|---|
| Ex. | | | |
| 1 | 10 | 110 | 9 Weeks |
| 2 | 12 | 160 | 6 Weeks |
| 3 | 8 | 60 | 10 Weeks |
| 4 | 10 | 120 | 9 Weeks |
| 5 | 11 | 170 | 9 Weeks |
| 6 | 6 | 20 | 11 Weeks |
| 7 | 11 | 200 | 9 Weeks |
| 8 | 11 | 120 | 10 Weeks |
| 9 | 10 | 110 | 10 Weeks |
| 10 | 10 | 100 | 9 Weeks |
| 11 | 9 | 90 | 9 Weeks |
| 12 | 9 | 110 | 9 Weeks |
| Comp. Ex. | | | |
| 1 | 10 | 80 | 3 Days |
| 2 | 8 | 10 | 1 Days |
| 3 | 9 | 20 | 7 Days |

EXAMPLE 14

Into a flask fitted with a thermometer and a forcedly rotated stirrer having two-stage propeller blades were charged 20 wt.% of cyclohexyl maleimide as the maleimide compound, 2 wt.% of partially saponified polyvinyl acetate as the protective colloid, 1 wt.% of polyoxyethylene nonylphenyl ether, with the number of moles of added oxyethylene equal to 5, as the surfactant, and 77 wt.% of water. The temperature of the flask-heating bath was raised to 89° C under stirring at 600 r.p.m. After cyclohexyl maleimide was dissolved in five minutes, the product was in the state of an aqueous emulsion. After about three minutes, the resulting aqueous emulsion was cooled to room temperature, under stirring for 30 minutes, to produce a homogeneous milk-white aqueous suspension.

The mean particle size of the maleimide compound in the produced aqueous suspension was then measured using a particle size distribution measuring device manufactured under the trade name of "MICRON PHOTOSIZER-SKC-2000" by SEISHIN KIGYO CO., LTD., while the particle size was measured at 20° C using a B-type viscometer. Then, regarding storage stability, each aqueous suspension was charged into a test tube having an inside diameter of 18 mm and a length of 18 cm, the test tube was placed stationarily in an incubator maintained at 25° C and the time which elapsed until water was separated by not less than 1 cm from the liquid surface was measured. The results are shown in Table 3.

EXAMPLES 15 TO 21

Samples of the aqueous suspensions of the maleimide compounds were prepared in the same way as in Example 14, except changing the operating conditions, the kinds and the amounts of the maleimide compounds, surfactants and the protective colloids and the types of the stirrers, as shown in Table 3, and measurements were conducted in the same way as in Example 14. The results are shown in Table 3.

EXAMPLE 22

Into a glass autoclave, fitted with a thermometer and a forcedly rotated stirrer equipped with two paddle-shaped blades, and covered with a heating jacket, there were charged 20 wt.% of N-methyl-α-methyl maleimide, as the maleimide compound, 2 wt.% of partially saponified polyvinyl acetate, as the protective colloid, 1 wt.% of sodium dodecylbenzene sulfonate, as the surfactant and 77 wt.% of water. After the temperature of the autoclave was raised to 120° C under stirring at 600 r.p.m., N-methyl-α-methyl maleimide was dissolved in about five minutes, and the product was in the state of an aqueous emulsion. After about three minutes, the resulting aqueous emulsion was cooled to room temperature, under stirring for 40 minutes, to produce a homogeneous milk-white aqueous suspension. Various measurements were then conducted of the produced samples of the aqueous suspension in the same way as in Example 14. The results are shown in Table 3.

COMPARATIVE EXAMPLE 4

An aqueous suspension was prepared in the same way as in Example 14 except pulverizing cyclohexyl maleimide as the maleimide compound into fine powders by a ball mill containing aluminum balls. Measurements were then conducted of the produced sample of the aqueous suspension in the same way as in Example 14. The results are shown in Table 3.

From the results of Table 3, the viscosity and the mean particle size of the aqueous suspension of the Comparative Example 4 were 15 poise and 15 μm, respectively. It was seen, however, that the suspension was partially flocculated and precipitation occurred as soon as the suspension was placed stationarily.

COMPARATIVE EXAMPLE 5

An aqueous suspension was prepared in the same way as in Example 14 except setting the temperature of the flask-heating bath to 59° c which is lower than the dissolving temperature of cyclohexyl maleimide, and setting the stirring time for the aqueous emulsion to 8 minutes. It was seen that precipitation occurred as soon as the suspension was placed stationarily so that a stable aqueous suspension could not be produced. Then, various measurements were conducted of the produced aqueous suspension in the same way as in Example 14. The results are shown in Table 3.

COMPARATIVE EXAMPLE 6

An aqueous suspension was prepared in the same way as in Example 14 except not using the protective colloid, and measurements were conducted in the same way as in Example 14. It was seen that, although the suspension remained stable directly after preparation, precipitation occurred in two days. The results are shown in Table 3.

TABLE 3

| No. | Ex. 14 | Ex. 15 | Ex. 16 | Ex. 17 |
|---|---|---|---|---|
| Maleimide Compounds, | Cyclohexylmaleimide | Benzylmaleimide | Phenylmaleimide | Ethylmaleimide |
| Content (Wt. %) | 20 | 5 | 10 | 60 |
| Water (Wt. %) | 77 | 93.5 | 84.8 | 29 |
| Kinds of Surfactants, | Polyoxyethylene Nonyl | Sodium Dodecylbenzene | Potassium Stearate | Lauric Acid Sorbitan |
| Content (Wt. %) | Phenyl Ether 1 | Sulfonate 0.5 | 0.2 | Ester 3 |
| Kinds of Protective | Partially Saponified | Partially Saponified | Carboymethyl Cellulose | Ethyl Cellulose |
| Colloids, Contents (Wt. %) | Polyvinyl Acetate 2 | Polyvinyl Acetate 1 | 5 | 8 |
| Kinds of Stirrers | Propeller Stirrer | Turbine Stirrer | Turbine Stirrer | Propeller Stirrer |
| Dispersion Temp. (°C.) | 89 | 70 | 90 | 50 |
| and Time (Min.) | 8 | 10 | 10 | 30 |
| Cooling Time (Min.) | 30 | 40 | 60 | 30 |
| Viscosity (Poise, 20° C.) | 20 | 5 | 10 | 40 |
| Mean Particle Size (μm) | 7 | 10 | 9 | 12 |
| Storage Stability (Weeks) | 6 | 10 | 8 | 3 |

| No. | Ex. 18 | Ex. 19 | Ex. 20 | Ex. 21 |
|---|---|---|---|---|
| Maleimide Compounds, | t-Butylmaleimide | Methylmaleimide | Laurylmaleimide | 2-Methylphenylmaleimide |
| Content (Wt. %) | 40 | 30 | 30 | 40 |
| Water (Wt. %) | 58.5 | 68 | 68.5 | 55 |
| Kinds of Surfactants, | Palmitic-acid | Sorbitan Monostearate | Sorbitan Monostearate | Dodecyl Trimethyl |
| Content (Wt. %) | Saccharose Ester 1 | 1 | 0.5 | Ammonium Chloride 2 |
| Kinds of Protective | Part. Saponified | Ethyl Cellulose | Ethyl Cellulose | Part. Saponified |
| Colloids, Contents (Wt. %) | Polyvinyl Acetate 0.2 | 1 | 1 | Polyvinyl Acetate 3 |
| Kinds of Stirrers | Homo-mixer | Homo-mixer | Turbo-mixer | Homogenizer |
| Dispersion Temp. (°C.) | 30 | 92 | 60 | 80 |
| and Time (Min.) | 5 | 10 | 20 | 5 |
| Cooling Time (Min.) | 40 | 40 | 30 | 40 |
| Viscosity (Poise, 20° C.) | 25 | 20 | 15 | 30 |
| Mean Particle Size (μm) | 10 | 6 | 5 | 3 |
| Storage Stability (Weeks) | 4 | 4 | 6 | 4 |

TABLE 3-continued

| No. | 22 | 4 | 5 | 6 |
|---|---|---|---|---|
| Maleimide Compounds, | N-Methyl-α- | Cyclohexylmaleimide | Cyclohexylmaleimide | Cyclohexylmaleimide |
| Content (Wt. %) | Methylmaleimide 20 | 20 | 20 | 20 |
| Water (Wt. %) | 77 | 77 | 77 | 77 |
| Kinds of Surfactants, | Sodium Dodeocyl- | Polyoxyethylene | Polyoxyethylene | Polyoxyethylene |
| Content (Wt. %) | benzensulfonate 1 | Nonylphenyl Ether 1 | Nonylphenyl Ether 1 | Nonylphenyl Ether 1 |
| Kinds of Protective | Part. Saponified | Part. Saponified | Part. Saponified | Part. Saponified |
| Colloids, Contents (Wt. %) | Polyvinyl Acetate 2 | Polyvinyl Acetate 2 | Polyvinyl Acetate 2 | Polyvinyl Acetate 2 |
| Kinds of Stirrers | Paddle Stirrer | Ball Mill | Propeller Stirrer | Propeller Stirrer |
| Dispersion Temp. (°C.) | 110 | 25 | 30 | 89 |
| and Time (Min.) | 5 | 30 | 8 | 8 |
| Cooling Time (Min.) | 40 | — | — | 30 |
| Viscosity (Poise, 20° C.) | 15 | 15 | — | 20 |
| Mean Particle Size (μm) | 9 | 10 | — | 7 |
| Storage Stability (Weeks) | 4 | Precipitated | Precipitated | Precipitated |

Although the present invention has been described with reference to the specific examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A maleimide composition of high stability comprising
   (a) 5 to 70 wt.% of a maleimide compound represented by the formula (I)

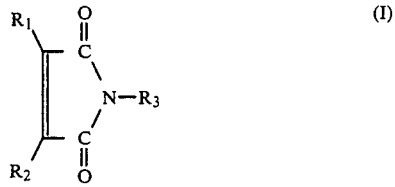

wherein $R_1$ and $R_2$ each stand for a hydrogen atom, a halogen atom or a methyl group, $R_3$ stands for a straight-chained or branched alkyl group having 1 to 18 carbon atoms, a halogen-substituted straight-chained alkyl group having 1 to 18 carbon atoms, a cycloalkyl group having 3 to 12 carbon atoms or an aryl or aralkyl group having 6 to 18 carbon atoms;
   (b) 0.1 to 20 wt.% of a surfactant;
   (c) 0.1 to 10 wt.% of a protective colloid; and
   (d) a balance of water.

2. A composition according to claim 1 wherein the maleimide compound represented by the formula (I) is selected from the group consisting of N-methyl maleimide, N-ethyl maleimide, N-n-propyl maleimide, N-n-butyl maleimide, N-t-butyl maleimide, N-i-butyl maleimide, N-n-pentyl maleimide, N-n-hexyl maleimide, N-cyclohexyl maleimide, N-n-heptyl maleimide, N-n-octyl maleimide, N-n-decyl maleimide, N-2-ethylhexyl maleimide, N-n-dodecyl maleimide, N n-tetradodecyl maleimide, N-n-hexadecyl maleimide, N-lauryl maleimide, N-myristyl maleimide, N-hexadecyl maleimide, N-octadecyl maleimide, N-phenyl maleimide, N-(2-methyl)phenyl maleimide, N-(4-t-butyl)phenyl maleimide, N-cumyl maleimide, N-(3-methyl)phenyl maleimide, N-(4-methyl)phenyl maleimide, N-(2-ethyl)phenyl maleimide, N-(2-chloro)phenyl maleimide, N-(3-chloro)phenyl maleimide, N-(4-chloro)phenyl maleimide, N-(2,4-dichloro)phenyl maleimide, N-(2-bromo)phenyl maleimide, N-(2-fluoro)phenyl maleimide, N-benzyl maleimide, N-methylbenzyl maleimide, N-methyl-α-chloromaleimide, N-methyl-α-methylmaleimide, N-methyl-α-bromomaleimide, N-methyl-α-fluoromaleimide, N-cyclohexyl-α-chloromaleimide, N-cyclohexyl-α-bromomaleimide, N-cyclohexyl-α,8-dichloromaleimide, N-cyclohexyl-α-methylmaleimide, N-phenyl-α-chloromaleimide, N-phenyl-α-methylmaleimide, N-benzyl-α-chloromaleimide, N-benzyl-α-methylmaleimide and mixtures thereof.

3. A composition according to claim 1 wherein said surfactant is selected from the group consisting of an anionic surfactant, a nonionic surfactant and mixtures thereof.

4. A composition according to claim 1 wherein said surfactant is a cationic surfactant.

5. A composition according to claim 3 wherein said anionic surfactant is selected from the group consisting of aliphatic acid salts, sulfonates, higher alcohol sulfuric acid ester salts, phosphates, sulfosuccinates, and mixtures thereof.

6. A composition according to claim 3 wherein said anionic surfactant is selected from the group consisting of sodium oleate, castor oil potassium soap, N-acylamino acid salts, alkyl ether carboxylates, alkyl sulfonates, sodium dodecylbenzene sulfonates, alkylnaphthalene sulfonates, derivatives of naphthalene sulfonates, sodium salts of β-naphthalene sulfonic acid formalin condensates, dialkyl sulfosuccinates, α-olefin sulfonates, N-acylsulfonates, sodium cetylsulfates, lauryl alcohol sodium sulfates, polyoxyethylene alkyl ether sulfates, polyoxyethylene alkyl phenol ether sulfates, alkylamide sulfates, alkyl phosphates, alkyl ether phosphates, alkyl allyl ether phosphoric acids, polycarboxylic acid, dialkyl esters of sodium sulfosuccinates, sodium alkylmethyl taurine, and mixtures thereof.

7. A composition according to claim 3 wherein said nonionic surfactant is selected from the group consisting of alkyl polyoxyethylene ethers, alkyl aryl polyoxyethylene ethers, condensed polyoxyethylene ethers, block and graft polymers having polyoxypropylene, polyoxyethylene ethers of glycerin esters, sorbitan esters, polyoxyethylene ethers of sorbitan esters, polyoxyethylene ethers of sorbitol esters, polyethyleneglycol fatty acid esters, glycerin esters, polyglycerin esters, propyleneglycol esters, mono-, di- and trisaccharide fatty acid esters, polyoxyethylene polyoxypropyrene block polymers, fatty acid alkanolamides, polyoxyethylene fatty acid amides and mixtures thereof.

8. A composition according to claim 4 wherein said cationic surfactant is selected from the group consisting of alkylamine hydrochlorates, alkyl trimethyl ammonium chlorides, alkyl dimethyl benzyl ammonium chlorides, polyoxyethylene alkyl amines and mixtures thereof 9. A composition according to claim 1 wherein said protective colloid is selected from the group consisting of water-soluble cellulose derivatives, partially saponified polyvinyl acetate, completely saponified polyvinyl acetate, polyvinyl pyrrolidone, polyacrylic acids, acrylic acid amides, acrylic acid copolymers of acrylic acid esters, carboxyvinyl polymers, gelatine, starch, agar and mixtures thereof.

* * * * *